United States Patent [19]
Amos et al.

[11] Patent Number: 5,412,094
[45] Date of Patent: May 2, 1995

[54] BICYCLIC BETA-LACTAM/PARABEN COMPLEXES

[75] Inventors: Jane G. Amos, Mooresville; Joseph M. Indelicato; Carol E. Pasini, both of Greenwood; Susan M. Reutzel, Indianapolis, all of Ind.

[73] Assignee: Eli Lilly and Company, Indianapolis, Ind.

[21] Appl. No.: 84,651

[22] Filed: Jun. 28, 1993

[51] Int. Cl.$^6$ .......................................... C07D 498/053
[52] U.S. Cl. ........................... 540/301; 540/215; 540/228; 540/205; 540/230
[58] Field of Search .............................. 540/301, 302

[56] References Cited

U.S. PATENT DOCUMENTS

| | | | |
|---|---|---|---|
| 3,531,481 | 9/1970 | Pfeiffer | 260/243 |
| 4,013,653 | 3/1977 | Wolfe | 260/244 R |
| 4,534,898 | 8/1985 | Shulabara et al. | 260/245.3 |
| 4,977,257 | 12/1990 | Eckrich et al. | 540/205 |

FOREIGN PATENT DOCUMENTS

| | | |
|---|---|---|
| 0311366 | 5/1988 | European Pat. Off. . |
| 0341991 | 10/1989 | European Pat. Off. . |
| 0369686 | 10/1989 | European Pat. Off. . |

OTHER PUBLICATIONS

Higuchi, T. et al., Investigation of Some Complexes Formed in Solution by Caffeine, Scientific Edition, 42, (138–145) (1953).

Primary Examiner—Nicholas Rizzo
Attorney, Agent, or Firm—Janet T. McClain; James J. Sales; Gerald V. Dahling

[57] ABSTRACT

The invention provides complexes of the formula:

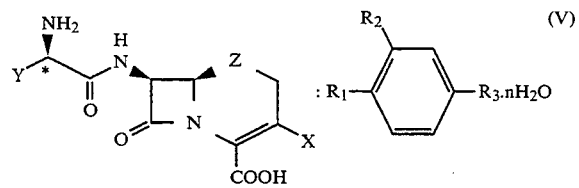

wherein
  X is chloro, hydrogen, vinyl, or —CH$_3$,
  Z is O;
  is 0–5;
  Y is phenyl or 1,4-cyclohexadien-1-yl;
  R$_1$ and R$_2$ are hydrogen or hydroxy, with the proviso that R$_1$ and R$_2$ are not both hydrogen and
  R$_3$ is —COO$^-$, —COO(C$_1$–C$_4$ alkyl), —NO$_2$ or

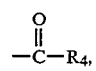

wherein R$_4$ is C$_1$–C$_4$ alkyl.

1 Claim, No Drawings

BICYCLIC BETA-LACTAM/PARABEN COMPLEXES

FIELD OF THE INVENTION

This invention relates to novel cephalosporin and carbacephalosporin/paraben complexes, and methods of use of such, particularly for isolation and purification of the β-lactam antibiotic.

BACKGROUND OF THE INVENTION

Cefaclor, cephalexin, cephradine and loracarbef have the structures as set out below:

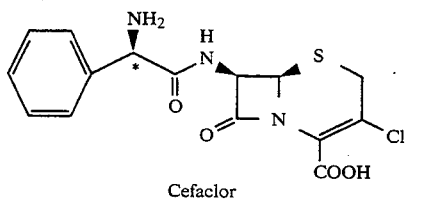

Cefaclor (I)

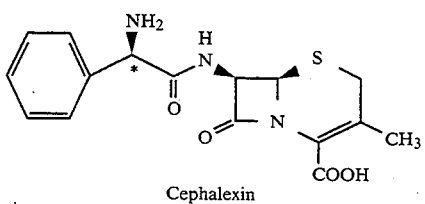

Cephalexin (II)

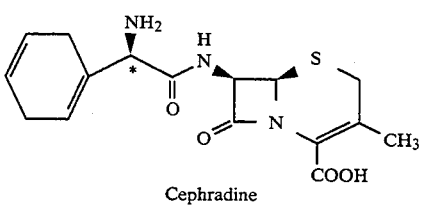

Cephradine (III)

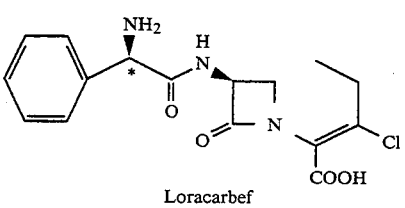

Loracarbef (IV)

The four β-lactam compounds, in which the C-2′ (*) asymmetric centers have the R absolute configuration, are commercially important oral antibiotics.

Various references discuss isolation and/or purification processes for the β-lactam compounds, such as that found in European Patent Application 0,341,991 published Nov. 15, 1989. In that EPO application is disclosed the use of anthraquinone-1,5-disulfonic acid to form a pharmaceutically acceptable salt with the particular cephalosporin or carbacephalosporin, which allows for recovery of the β-lactam from mother liquors after crystallization.

As these antibiotics are expensive to make, new and improved procedures for such recovery are continually being sought in order to maximize overall yield.

SUMMARY OF THE INVENTION

The commercially important antibiotics cephalexin, cefaclor, cephradine and loracarbef have been observed to form crystalline complexes with parabens and related compounds. The present invention is directed to complexes of the formula

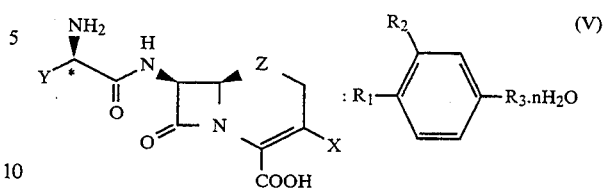

wherein
X is chloro, hydrogen, vinyl or —CH$_3$,
Z is CH$_2$, S, or O;
n is 0–5;
Y is phenyl or 1,4-cyclohexadien-1-yl;
R$_1$ and R$_2$ are hydrogen or hydroxy, with the proviso that R$_1$ and R$_2$ are not both hydrogen and
R$_3$ is CO$_2$H, —COO(C$_1$-C$_4$ alkyl), —NO$_2$ or

wherein R$_4$ is C$_1$–C$_4$ alkyl.

Further, the invention is directed to the formation of the above complexes in order to recover antibiotic material.

DESCRIPTION OF THE INVENTION

The terms "complex" and "cocrystal" are used to describe the single solid state phase resulting from the combination of the antibiotic and the paraben or related compound.

The preparation and isolation of cephalexin, cefaclor, cephradine, or loracarbef paraben complexes are simple and straightforward. Aqueous and substantially aqueous solutions or suspensions of the β-lactam and paraben or related compound are mixed and the components are allowed to co-crystallize at a temperature in the range of 0° to 65° C. The preferred amount of paraben or related compound added is 1 to 3 equivalents per equivalent of β-lactam used.

In each case, formation of cocrystals was demonstrated by its unique X-ray powder pattern which differs from the published X-ray powder patterns for cephalexin (L. P. Marelli, Analytical Profiles of Drug Substances, 4, pp. 21–46 (1975)); cephradine (K. Florey, Analytical Profiles of Drug Substances, 5, pp. 21–59 (1976)); cefaclor (L. S. Lorenz, Analytical Profiles of Drug Substances, 9, pp. 107–123 (1980)); loracarbef monohydrate [Pasini, European Patent Application EP 0311366 A1, published Apr. 12, 1989) and loracarbef dihydrate (Eckrich et al., European Patent Application 0369686 A1, published May 23, 1990); methyl, ethyl, and propyl paraben, methyl 3-hydroxybenzoate and acetophenones.

Neither cefadroxil, nor the arylglycine penicillins, amoxicillin and ampicillin, formed appreciable levels of either methyl or propyl paraben cocrystals in our laboratory.

Crystalline complexes of the β-lactams with parabens and related compounds may be used in recovery, isolation, and/or purification processes of the β-lactam. The cocrystals can be used to precipitate the β-lactam from dilute solutions (for example mother liquors or reaction solutions). The cocrystals can be isolated by filtration. To recover the β-lactam, the cocrystals can be dissolved in an acidic organic solvent or an acidic aqueous organic solvent system. Suitable acids are known in the art and include, for example, hydrochloric, sulfuric and hydrobromic acids. Suitable solvents include ethanol, n-butanol, methyl isobutyl ketone, diethyl ether, diisopropyl ether, ethyl acetate, methylene chloride, tetrahydrofuran, dimethylformamide, dimethylsulfoxide, and aqueous mixtures thereof. The β-lactam is isolated from the resulting solution by raising the pH of the mixture to precipitate the β-lactam while the paraben or related compound remains in solution. Suitable bases are known in the art and include ammonium hydroxide, sodium hydroxide, and triethylamine. The isolation of the β-lactam may take place between 0°–50° C. Alternatively, the cocrystals may be dissolved in a basic organic solvent or basic organic aqueous solvent system and the β-lactam precipitated by lowering the pH. In either case, the β-lactam is collected by filtration and may be used as is or converted to a more desirable crystal form.

EXPERIMENTALS

General Methods

Table 1, illustrates the X-ray powder diffraction patterns for the products of Examples 1–5, wherein "d" is the interplanar spacing and is measured in Angstroms and "$I/I_0$" is the relative intensity.

TABLE I

| Cephalexin: Methyl Paraben $H_2O$ | | Cephradine: Methyl Paraben $H_2O$ | | Loracarbef: Propyl Paraben | | Loracarbef: Methyl Paraben | | Cefaclor: Methyl Paraben 3 $H_2O$ | |
|---|---|---|---|---|---|---|---|---|---|
| d (Å) | $I/I_0$ | d (Å) | $I/I_0$ | d (Å) | $I/I_0$ | d (Å) | $I/I_0$ | d (Å) | $I/I_0$ |
| 12.40 | 100 | 12.49 | 100 | 12.36 | 46 | 11.89 | 100 | 13.62 | 61 |
| 10.77 | 43 | 10.77 | 43 | 9.33 | 21 | 10.54 | 12 | 10.18 | 59 |
| 7.48 | 6 | 7.51 | 4 | 9.08 | 5 | 8.82 | 29 | 9.99 | 83 |
| 7.10 | 6 | 7.14 | 4 | 7.59 | 8 | 7.21 | 20 | 8.88 | 20 |
| 6.31 | 17 | 6.33 | 12 | 7.04 | 6 | 6.97 | 17 | 8.77 | 25 |
| 6.09 | 9 | 6.13 | 7 | 6.72 | 7 | 6.24 | 13 | 8.17 | 10 |
| 6.01 | 22 | 6.00 | 19 | 6.12 | 39 | 5.97 | 16 | 6.67 | 18 |
| 5.55 | 66 | 5.54 | 74 | 5.63 | 8 | 5.90 | 13 | 6.59 | 11 |
| 5.11 | 25 | 5.00 | 25 | 5.17 | 48 | 5.69 | 33 | 6.27 | 100 |
| 4.79 | 27 | 4.79 | 23 | 4.86 | 40 | 5.47 | 27 | 5.76 | 25 |
| 4.69 | 13 | 4.68 | 7 | 4.67 | 17 | 5.33 | 18 | 5.52 | 19 |
| 4.49 | 11 | 4.51 | 10 | 4.51 | 7 | 5.16 | 9 | 5.37 | 61 |
| 4.42 | 21 | 4.43 | 15 | 4.39 | 39 | 5.09 | 8 | 5.02 | 55 |
| 4.33 | 29 | 4.34 | 20 | 4.31 | 24 | 4.75 | 50 | 4.87 | 47 |
| 4.29 | 9 | 4.26 | 5 | 4.22 | 12 | 4.64 | 63 | 4.50 | 28 |
| 4.13 | 35 | 4.13 | 25 | 4.09 | 51 | 4.57 | 61 | 4.39 | 9 |
| 4.10 | 54 | 4.10 | 57 | 3.99 | 7 | 4.39 | 21 | 4.28 | 20 |
| 4.03 | 8 | 4.05 | 9 | 3.58 | 100 | 4.28 | 27 | 4.11 | 79 |
| 3.86 | 40 | 3.95 | 5 | 3.54 | 9 | 4.17 | 26 | 4.00 | 29 |
| 3.75 | 13 | 3.87 | 32 | 3.45 | 11 | 4.10 | 19 | 3.93 | 34 |
| 3.73 | 14 | 3.76 | 13 | 3.36 | 8 | 3.96 | 60 | 3.78 | 12 |
| 3.64 | 11 | 3.72 | 29 | 3.26 | 17 | 3.92 | 46 | 3.73 | 33 |
| 3.60 | 16 | 3.64 | 9 | 3.12 | 14 | 3.79 | 12 | 3.54 | 84 |
| 3.54 | 9 | 3.60 | 13 | 3.07 | 15 | 3.61 | 87 | 3.49 | 34 |
| 3.47 | 11 | 3.54 | 8 | 2.92 | 17 | 3.49 | 25 | 3.44 | 25 |
| 3.41 | 10 | 3.47 | 9 | 2.9 | 6 | 3.36 | 33 | 3.35 | 64 |
| 3.36 | 12 | 3.41 | 10 | 2.82 | 5 | 3.13 | 19 | 3.30 | 97 |
| 3.31 | 6 | 3.36 | 13 | 2.68 | 12 | 3.00 | 21 | 3.21 | 36 |
| 3.23 | 12 | 3.31 | 5 | 2.57 | 12 | 2.88 | 15 | 3.18 | 66 |
| 3.16 | 40 | 3.23 | 9 | 2.54 | 6 | 2.80 | 21 | 3.15 | 16 |
| 3.08 | 20 | 3.16 | 28 | 2.43 | 10 | 2.72 | 20 | 3.09 | 14 |
| 3.06 | 18 | 3.07 | 21 | 2.38 | 11 | 2.70 | 19 | 3.06 | 20 |
| 3.03 | 15 | 3.02 | 17 | 2.18 | 5 | 2.64 | 17 | 3.03 | 35 |
| 2.97 | 8 | 2.97 | 8 | | | 2.55 | 16 | 3.00 | 31 |
| 2.92 | 10 | 2.93 | 8 | | | 2.29 | 16 | 2.97 | 24 |
| 2.89 | 7 | 2.89 | 11 | | | 2.24 | 15 | 2.93 | 48 |
| 2.76 | 12 | 2.85 | 5 | | | 2.03 | 14 | 2.86 | 12 |
| 2.69 | 12 | 2.77 | 13 | | | | | 2.85 | 10 |
| 2.67 | 9 | 2.71 | 6 | | | | | 2.77 | 47 |
| 2.58 | 6 | 2.68 | 13 | | | | | 2.74 | 15 |
| 2.55 | 9 | 2.67 | 9 | | | | | 2.69 | 21 |
| 2.53 | 9 | 2.58 | 7 | | | | | 2.67 | 19 |
| 2.50 | 10 | 2.55 | 10 | | | | | 2.64 | 9 |
| 2.46 | 12 | 2.54 | 6 | | | | | 2.61 | 14 |
| 2.45 | 8 | 2.52 | 4 | | | | | 2.56 | 27 |
| 2.37 | 16 | 2.50 | 7 | | | | | 2.52 | 31 |
| 2.32 | 11 | 2.46 | 13 | | | | | 2.49 | 14 |
| 2.28 | 10 | 2.44 | 6 | | | | | 2.43 | 20 |
| 2.28 | 9 | 2.37 | 14 | | | | | 2.41 | 13 |
| 2.25 | 18 | 2.35 | 13 | | | | | 2.36 | 16 |
| 2.17 | 6 | 2.32 | 10 | | | | | 2.33 | 10 |
| 2.11 | 6 | 2.28 | 9 | | | | | 2.30 | 26 |
| 2.07 | 10 | 2.25 | 11 | | | | | 2.29 | 16 |
| 2.05 | 9 | 2.18 | 5 | | | | | 2.26 | 12 |
| | | 2.11 | 5 | | | | | 2.24 | 21 |
| | | 2.09 | 4 | | | | | 2.22 | 21 |
| | | 2.07 | 8 | | | | | 2.20 | 12 |
| | | 2.05 | 5 | | | | | 2.17 | 19 |
| | | 2.15 | 33 | | | | | | |
| | | 2.12 | 8 | | | | | | |
| | | 2.10 | 13 | | | | | | |

TABLE I-continued

| Cephalexin: Methyl Paraben H$_2$O | | Cephradine: Methyl Paraben H$_2$O | | Loracarbef: Propyl Paraben | | Loracarbef: Methyl Paraben | | Cefaclor: Methyl Paraben 3 H$_2$O | |
|---|---|---|---|---|---|---|---|---|---|
| d (Å) | I/I$_0$ | d (Å) | I/I$_0$ | d (Å) | I/I$_0$ | d (Å) | I/I$_0$ | d (Å) | I/I$_0$ |
| | | 2.08 | 17 | | | | | | |
| | | 2.03 | 10 | | | | | | |

EXAMPLE 1

Cephalexin:Methyl Paraben•H$_2$O

Methyl paraben (375 mg, 2.5 mmol) in 150 ml of water was added to cephalexin monohydrate (2.4 g, 6.6 mmol) to result in a suspension. After 5 days at 5° C., the crystals were collected by filtration and washed with water to give 1.06 g (2.0 mmol) of cocrystals. mp 168°–169° C. Anal. calcd for $C_{24}H_{25}N_3O_7S \cdot H_2O$: C, 55.70; H, 5.26; N, 8.12. Found: C, 55.65; H, 5.28; N, 8.13. HPLC assay (calcd), found: (67.1), 67.1% cephalexin, (29.4), 28.7% methyl paraben. KF (Calcd), found: (3.5), 4.0% water.

EXAMPLE 2

Cephradine:Methyl Paraben•H$_2$O

Methyl paraben (250 mg, 1.6 mmol) in 100 ml of water was added to cephradine monohydrate (1.6 g, 4.4 mmol) to result in a suspension. After 3 days at 25° C., the crystals were collected by filtration and washed with water to yield 0.609 g (1.2 mmol) of cocrystals with 1 mol of water of crystallization. mp 167°–168° C. Anal.-calcd for $C_{24}H_{27}N_3O_7S \cdot H_2O$: C, 55.48; H, 5.63; N, 8.09. Found: C, 55.58; H, 5.57; N, 8.08. HPLC assay (calcd), found: (67.2), 67.7% cephradine, (29.3), 28.9% methyl paraben. KF (calcd), found: (3.5), 3.7% water.

EXAMPLE 3

Cefaclor:Methyl Paraben•3H$_2$O

Methyl paraben (250 mg, 1.6 mmol) in 100 ml of water was added to cefaclor monohydrate (1.3 g, 3.4 mmol) to give a suspension. After 5 days at 5° C., the crystals were collected by filtration and washed with water to give cocrystals with 3 mol of water of crystallization, mp 142° C. dec. Anal.-calcd for $C_{23}H_{22}ClN_3O_7S \cdot 3H_2O$: C, 48.13; H, 4.92; N, 7.32. Found: C, 48.01; H, 4.92; N, 6.99. HPLC as say (calcd), found: (64.1), 65.0% cefaclor, (26.5), 25.4% methyl paraben. KF (Calcd), found: (9.4), 9.9% water.

EXAMPLE 4

Loracarbef:Methyl Paraben

Methyl paraben (460 mg, 3.0 mmol) in 230 ml of water was added to loracarbef monohydrate (3.0 g, 8.2 mmol) to give a suspension. After 25 days at 25° C. the crystals were isolated by filtration and washed with water to give 0.72 g (1.4 mmol) of cocrystals. mp 191° C. dec. Anal.calcd for $C_{24}H_{24}C_1N_3O_7$: C, 57.44; H, 4.82; N, 8.37. Found: C, 57.16; H, 4.92; N, 8.59. HPLC assay (Calcd), found: (69.7), 70.6% loracarbef, (30.3), 30.0% methyl paraben.

EXAMPLE 5

Loracarbef:Propyl Paraben

Propyl paraben (500 mg, 2.8 mmol) in 500 ml of water was added to loracarbef monohydrate (5.5 g, 14.9 mmol) to give a suspension. After 20 days at 5° C., the crystals were recovered by filtration and washed with water to yield 1.31 g (2.5 mmol) of cocrystals. mp 178° C. dec. Anal. Calcd. for $C_{26}H_{28}C_1N_3O_7$: C, 58.92; H, 5.32; N, 7.93. Found: C, 58.69; H, 5.31; N, 7.90. HPLC assay (calcd), found: (66.0), 64.31% loracarbef, (34.0), 33.3% propyl paraben.

EXAMPLE 6

Loracarbef:Ethyl Paraben

The pH of aqueous loracarbef monohydrate mother liquor (1000 ml, having 9.23 mg/ml of loracarbef monohydrate) was adjusted to 3.6 with HCl. Ethyl p-hydroxybenzoate (ethyl paraben) (4.52g) in ethanol (36 ml) was added dropwise over 15 minutes. After approximately 5 minutes, precipitation occurred, resulting in white crystals. The mixture was stirred overnight (15 hrs) at room temperature, filtered, washed with H$_2$O, and dried under vacuum at 40° C. The yield was 11.72 g having a potency of 73.5% as loracarbef, and the theoretical yield was 8.78 g as loracarbef, resulting in a percent yield of 98.2%. The loracarbef:ethyl paraben exhibited the following X-ray powder diffraction pattern:

| d | (I/I$_0$) |
|---|---|
| 12.03778 | 100.0 |
| 10.51978 | 2.7 |
| 8.87879 | 28.6 |
| 7.24748 | 4.0 |
| 6.04328 | 1.6 |
| 5.77434 | 39.3 |
| 5.27012 | 2.9 |
| 4.95456 | 3.6 |
| 4.80014 | 0.6 |
| 4.60833 | 2.7 |
| 4.50920 | 2.6 |
| 4.03255 | 38.1 |
| 3.57845 | 38.9 |
| 3.54171 | 4.3 |
| 3.35279 | 22.4 |
| 3.20988 | 1.4 |
| 3.16843 | 0.7 |
| 3.02715 | 4.6 |
| 2.89099 | 3 9 |
| 2.83791 | 0.5 |
| 2.80444 | 1.0 |
| 2.76760 | 1.9 |
| 2.69465 | 1.5 |
| 2.62614 | 1.6 |

EXAMPLE 7

Loracarbef:Methyl 3-Hydroxybenzoate•5H$_2$O

Methyl 3-hydroxybenzoate (496 mg, 3.3 mmol) in 3 ml of EtOH was added to loracarbef monohydrate (1.2 g, 3.3 mmol) in 200 ml of water. After 19 days at 25° C., the crystals were collected by filtration and washed with water to yield 576 mg (0.97 mmol) of cocrystals. Anal, calcd for $C_{24}H_{24}C_1N_3O_7 \cdot 5H_2O$: C, 48.69; H, 5.79; N, 7.10. Found: C, 48.84; H. 5.56; N, 7.23.

EXAMPLE 8

Loracarbef:Methyl Paraben

Loracarbef ethanolate (2.55 g, 74.7% as loracarbef) was suspended in 100 ml of $H_2O$. NaOH (1.0 N, 1.08 ml) was added, and the pH was raised to 8.9. The mixture was stirred until the loracarbef was almost dissolved. Methyl p-hydroxybenzoate (methyl paraben) (0.83 g) in 7 ml of ethanol was added, and the pH dropped to 8.1 within several minutes. The mixture became turbid as the solid began to precipitate. The mixture was stirred at room temperature for 2 hours, filtered, washed with $H_2O$ and dried overnight under vacuum at 40° C. The yield was 1.92 g, the theoretical yield as cocrystal was 2.83 g, with a percent yield of 67.8%.

EXAMPLE 9

Loracarbef:Butyl Paraben

Loracarbef ethanolate (2.55 g, 74.6% as loracarbef) was added to 100 ml of $H_2O$. The pH was adjusted to 8.4 with NaOH (1.0M, 1.08 ml). After stirring for 30 minutes at room temperature, the solution was almost clear. Butyl p-hydroxybenzoate (butyl paraben) (1.06g) in 7 ml ethyl alcohol was added to the mixture. The mixture was stirred for several hours at room temperature, filtered, washed with $H_2O$ and dried under vacuum of 40° C. The titled product was white. The actual yield was 1.78 g, the theoretical yield was 3.06 g as cocrystal with a percent yield of 58.2%.

EXAMPLE 10

Loracarbef:Ethyl paraben

Loracarbef ethanolate (2.55 g, 74.7% as loracarbef) was suspended in 100 ml $H_2O$. NaOH in a molar excess was added, the pH rose to 8.4, and a clear mixture was obtained. Ethyl p-hydroxybenzoate (0.90 g, 5.44 mm) in 7 ml ethyl alcohol was added to the mixture, and within several minutes a thick precipitate formed. The pH was 9.95. The mixture was stirred several hours at room temperature, filtered, washed with $H_2O$ and dried under vacuum at 40° C. The actual yield was 2.08 g, the theoretical yield as cocrystal was 2.90 g, and the % yield was 71.7%.

EXAMPLE 11

Loracarbef:Pyropyl Paraben

Loracarbef ethanolate (2.55 g, 74.7% as loracarbef) was suspended in 100 ml $H_2O$. NaOH (1 N, 1.08 ml) was added and the pH was 7.2. A further amount of 1N NaOH was added to raise the pH to 8.2. Propyl p-hydroxybenzoate (0.90 g, 5.44 mm) in 7 ml ethyl alcohol was added to the mixture, and immediately a white solid precipitated. The mixture was stirred at room temperature for several hours. The mixture was filtered, washed with $H_2O$ and dried under vacuum at 40° C. The pH of the filtrate was lowered to 4.9, but no additional precipitation was observed. The actual yield was 0.90 g, the theoretical yield as cocrystal was 2.98 g, and the % yield was 30.2%.

EXAMPLE 12

Loracarbef:Ethyl Paraben

An acylation reaction was run according to U.S. Pat. Nos. 4,316,958, 4,332,896 and 4,335,211. The acylation reaction mixture was extracted with methylene chloride and the aqueous phase filtered. Ethyl paraben (3.82 g) was dissolved in 3 ml of ethyl alcohol and added to the aqueous solution containing 4.23 g of loracarbef as the monohydrate. The solution began to crystallize and the pH was lowered to 4.3 with hydrochloric acid. The mixture was stirred for several hours at room temperature. The mixture was cooled overnight in a refrigerator, filtered, washed with water, and dried under vacuum at 45° C. The actual yield was 8.37 g, 39% potency as loracarbef, the theoretical yield was 3.99 g as loracarbef and the % yield was 81.2%.

EXAMPLE 13

Loracarbef:Ethyl Paraben

Ethyl paraben (3.50 g) was dissolved in 30 ml of ethyl alcohol and added to aqueous loracarbef monohydrate (3.88 g, 10.55 mm). The pH was lowered to 3.5 with hydrochloric acid and the suspension was stirred for several hours at room temperature. The suspension was cooled to 5° C. for several hours, filtered, and dried under vacuum at 55° C. The actual yield was 6.35 g, 55.3%, potency as loracarbef, the theoretical yield was 3.69 g, and the % yield was 95.1%.

EXAMPLE 14

Loracarbef DMF Disolvate

To a mixture of loracarbef: ethyl paraben (1.34 g, 65.5% potency as loracarbef) in 18 ml of DMF and 1.8 ml of $H_2O$ was added concentrated hydrochloric acid sufficient to obtain a clear solution. The pH of the solution was slowly raised to 6.9 with triethylamine, and the crystallization of the titled product occurred quickly. The mixture was stirred for 1 hour at room temperature, filtered, washed with a solution of 10:1/DMF:$H_2O$, and dried under a vacuum at 40° C. HPLC analysis indicated that no ethyl paraben was present. The actual yield was 1.01 g, 73.9% potency as loracarbef, the theoretical yield was 0.87 g as loracarbef, and the percent yield was 85.3%.

EXAMPLE 15

Loracarbef DMF Disolvate

To loracarbef:ethyl paraben (15.0 g, 49.1% potency as loracarbef), predisolved in 150 ml DMF and 15 ml $H_2O$ was added concentrated hydrochloric acid (2.53 ml) dropwise. The solution was heated to 45° C. and the pH was raised from 1.84 to 4.0 over 45 minutes using triethylamine. After crystallization began, triethylamine was slowly added until a pH of 6.7 was obtained. The mixture was stirred for 1 hour at 45° C., filtered, washed with DMF and ethanol and dried under vacuum at 40° C. HPLC analysis indicated that no ethyl paraben was present. The actual yield was 10.07 g, 72% as loracarbef activity, the theoretical yield was 7.37 g of loracarbef activity, and the percent yield was 98.4% yield.

EXAMPLE 16

Loracarbef

Loracarbef:ethyl paraben (3.0 g, 49.1% as loracarbef) was suspended in 30 ml of 1:1 acetonitrile:$H_2O$. The pH of the mixture was lowered to 1.9 with concentrated hydrochloric acid at which time a clear solution was obtained. The pH of the mixture was raised to 4.9 using triethylamine and a white precipitate formed quickly. The mixture was stirred for 1 hour, at room temperature, filtered, washed with 1:1/acetonitrile:$H_2O$, and dried under vacuum at 45° C. The actual yield was 1.36 g, 98.1% potency as loracarbef, the theoretical yield was 1.47 g, and the percent yield was 90.3%.

EXAMPLE 17

Loracarbef Ethanolate

Loracarbef:ethyl paraben (11.26 g, 72.9% as loracarbef) was suspended in 90 ml of ethyl alcohol and 9 ml of $H_2O$. Hydrochloric acid (3.5 ml) was added to obtain a clear solution, and the pH was approximately 0.80. To the mixture was added 5.0 ml of Eriethylamine in 30 ml of ethanol. The mixture was stirred for two hours, filtered, washed with ethanol, and dried under vacuum at 40° C. The actual yield was 8.22 g, 94.8% as loracarbef, the theoretical yield was 8.21 g, and the percent yield was 95.0%.

EXAMPLE 18

Loracarbef Monohydrate

Loracarbef:ethyl paraben (30.0 g, 72.7% as loracarbef) was suspended in 240 ml of ethyl alcohol and 24 ml of $H_2O$. To this mixture was added 9.0 ml of concentrated hydrochloric acid to obtain a clear solution. To the mixture, 15 ml of triethylamine and 84 ml of ethyl alcohol was added. The mixture was stirred for 1 hour at room temperature, filtered, and washed with ethanol, and dried under vacuum at 40° C. to result in the loracarbef ethanolate. The actual yield of the loracarbef ethanolate was 22.59 g, 86.2% potency as loracarbef, the theoretical yield was 21.81 g of loracarbef activity, and the percent yield was 89.3%.

Loracarbef ethanolate (5.0 g, 86.2%, potency as loracarbef), from above was suspended in 70 ml of $H_2O$, and the slurry was heated to 50° C. The slurry became very thick which indicated conversion to the monohydrate. The slurry was stirred at 50° C. for 1 hour, filtered, washed with $H_2O$ and dried under vacuum at 40° C. The actual yield of loracarbef monohydrate was 3.06 g, 102.8% potency as loracarbef monohydrate, the theoretical yield was 4.53 g, and the percent yield was 69.3%.

EXAMPLE 19

Cefaclor:4-Hydroxyacetophenone

A solution of 265 mg (1.94 mmol) of 4-hydroxyacetophenone in 1 ml of ethanol was added to 750 mg (1.94 mmol)) of cefaclor monohydrate predissolved in 81 ml of water. The turbid solution was covered and allowed to stand at room temperature overnight, after which time very large, pale yellow crystals were recovered by filtration. mp 198°–203° C. (dec). %CHN calcd for $C_{23}H_{22}ClN_3O_6S$: C,54.81; H, 4.36; N, 8.34. Found C, 54.95; H, 4.51: N, 8.63. The cefaclor:4-hydroxyacetophenone exhibited the following X-ray powder diffraction pattern:

| d | (I/I$_0$) |
| --- | --- |
| 11.4958 | 100.00 |

-continued

| d | (I/I$_0$) |
| --- | --- |
| 10.1960 | 10.80 |
| 8.7598 | 16.87 |
| 7.3321 | 10.70 |
| 6.9139 | 8.61 |
| 6.8571 | 6.32 |
| 6.4493 | 7.76 |
| 5.6711 | 89.55 |
| 5.5743 | 30.10 |
| 5.1132 | 10.55 |
| 4.9524 | 11.19 |
| 4.8824 | 13.13 |
| 4.7479 | 63.18 |
| 4.5850 | 26.57 |
| 4.5361 | 45.42 |
| 4.3973 | 27.41 |
| 4.3076 | 17.56 |
| 4.1818 | 5.97 |
| 4.1310 | 7.86 |
| 4.0050 | 41.00 |
| 3.9243 | 30.40 |
| 3.8845 | 37.66 |
| 3.6794 | 14.88 |
| 3.5963 | 22.29 |
| 3.5070 | 42.29 |
| 3.4101 | 11.74 |
| 3.3658 | 14.28 |
| 3.3072 | 46.17 |
| 3.2420 | 49.50 |
| 3.1725 | 13.58 |
| 3.1421 | 14.48 |
| 3.0758 | 10.95 |
| 3.0452 | 11.29 |
| 2.9962 | 13.28 |
| 2.9223 | 59.60 |
| 2.8845 | 15.67 |
| 2.8232 | 14.38 |
| 2.7527 | 14.63 |
| 2.7286 | 7.46 |
| 2.6418 | 21.14 |
| 2.5815 | 14.73 |

We claim:
1. A complex of the formula

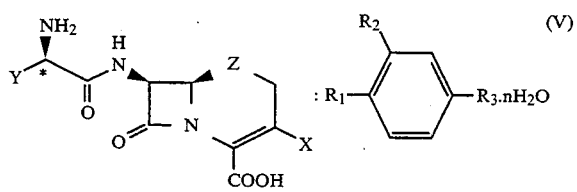

wherein
X is chloro, hydrogen, vinyl, or —$CH_3$,
Z is O;
n is 0 to 5;
Y is phenyl or 1,4-cyclohexadien-1-yl;
$R_1$ and $R_2$ are hydrogen or hydroxy, with the proviso that $R_1$ and $R_2$ are not both hydrogen and
$R_3$ is —$CO_2H$, —$COO(C_1-C_4$ alkyl), —$NO_2$ or,

wherein $R_4$ is $C_1$—$C_4$ alkyl.

* * * * *

UNITED STATES PATENT AND TRADEMARK OFFICE
CERTIFICATE OF CORRECTION

PATENT NO. : 5,412,094
DATED : May 2, 1995
INVENTOR(S) : Jane G. Amos, et al.

Page 1 of 2

It is certified that error appears in the above-indentified patent and that said Letters Patent is hereby corrected as shown below:

Column 1, lines 40-48, "

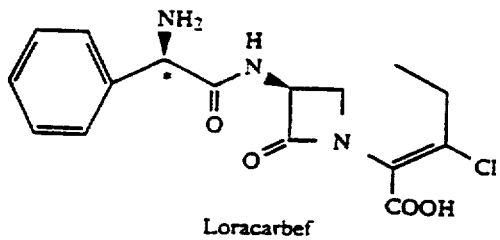

should read,
--

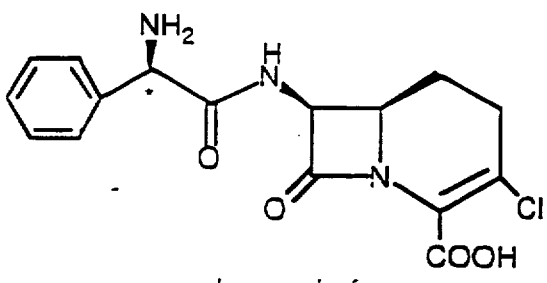
--

Column 5, line 11, "Ceohalexin:Methyl" should read, -- Cephalexin:Methyl --.
Column 5, line 38, "Cemaclor:Methyl" should read, -- Cefaclor:Methyl --.
Column 5, line 58, "$C_{24}H_{24}C_{1}N_{3}O_{7}$" should read, -- $C_{24}H_{24}ClN_{3}O_{7}$ --.
Column 5, line 62, "Propyl Parahen" should read, -- Propyl Paraben --.
Column 6, line 15, "$C_{26}H_{28}C_{1}N_{3}O_{7}$" should read, -- $C_{26}H_{28}ClN_{3}O_{7}$ --.
Column 6, line 63, "ml of EtOH" should read, -- ml of 95% EtOH --.
Column 6, line 67, "$C_{24}H_{24}C_{1}N_{3}O_{7}$" should read, -- $C_{24}H_{24}ClN_{3}O_{7}$ --.

UNITED STATES PATENT AND TRADEMARK OFFICE
CERTIFICATE OF CORRECTION

PATENT NO. : 5,412,094
DATED : May 2, 1995
INVENTOR(S) : Jane G. Amos, et al.

It is certified that error appears in the above-indentified patent and that said Letters Patent is hereby corrected as shown below:

Column 9, line 11, "Eriethylamine" should read --triethylamine--.

Signed and Sealed this

Tenth Day of October, 1995

Attest:

BRUCE LEHMAN

Attesting Officer

Commissioner of Patents and Trademarks